(12) United States Patent
Nawata

(10) Patent No.: US 7,954,493 B2
(45) Date of Patent: *Jun. 7, 2011

(54) OXYGEN SUPPLYING APPARATUS

(75) Inventor: Hideo Nawata, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 987 days.

This patent is subject to a terminal disclaimer.

(21) Appl. No.: 10/524,632

(22) PCT Filed: Dec. 16, 2003

(86) PCT No.: PCT/JP03/16122
§ 371 (c)(1),
(2), (4) Date: Feb. 16, 2005

(87) PCT Pub. No.: WO2004/054648
PCT Pub. Date: Jan. 7, 2004

(65) Prior Publication Data
US 2006/0048781 A1 Mar. 9, 2006

(30) Foreign Application Priority Data
Dec. 17, 2002 (JP) .................................. 2002-365195

(51) Int. Cl.
*F16K 31/02* (2006.01)
*A62B 9/02* (2006.01)

(52) U.S. Cl. .......... 128/204.23; 128/204.21; 128/205.24

(58) Field of Classification Search ............. 128/205.11, 128/205.12, 204.18, 204.21, 204.23, 204.25, 128/204.26, 205.24; 95/96
See application file for complete search history.

(56) References Cited

U.S. PATENT DOCUMENTS
3,221,734 A * 12/1965 Beasley ................... 128/204.28

(Continued)

FOREIGN PATENT DOCUMENTS
EP 0188071 A1 7/1986

(Continued)

OTHER PUBLICATIONS

International Search Report mailed on Mar. 9, 2004.

(Continued)

*Primary Examiner* — Kristen C Matter
(74) *Attorney, Agent, or Firm* — Rader, Fishman & Grauer PLLC

(57) ABSTRACT

As a respiration synchronized-type gas supplying apparatus which has a function for setting the flow rate during continuous supply and at the same time can be miniaturized by simplifying the structure, the present invention provides an oxygen supplying apparatus comprising an oxygen generating means, an oxygen supplying means for supplying the oxygen generated by the oxygen supplying means to a user and an automatic closing valve placed on the oxygen-supplying passage, wherein the oxygen supplying apparatus is provided with the following: a respiration sensor which detects the respiration of a user; a supply method setting means which selects the supply in a continuous flow or the supply in synchronism with the respiration of the user; a flow rate setting means for a supply flow rate; and a controlling means which controls the aperture of the closing valve corresponding to the set value of the flow rate setting means by receiving a supply method setting signal of the continuous flow, or opens the automatic closing valve on the inhalation starting point based on the respiration signal of the respiration sensor by receiving a supply method setting signal of the synchronous flow and at the same time controls the open time of the automatic closing valve corresponding to the flow rate set value.

8 Claims, 3 Drawing Sheets

U.S. PATENT DOCUMENTS

| | | | |
|---|---|---|---|
| 4,648,395 A | 3/1987 | Sato et al. | |
| 4,681,099 A * | 7/1987 | Sato et al. | 128/204.23 |
| 4,822,384 A * | 4/1989 | Kato et al. | 96/110 |
| 5,398,676 A * | 3/1995 | Press et al. | 128/204.23 |
| 5,540,220 A * | 7/1996 | Gropper et al. | 128/204.23 |
| 5,603,315 A | 2/1997 | Sasso, Jr. | |
| 6,000,396 A * | 12/1999 | Melker et al. | 128/204.21 |
| 2002/0038656 A1 | 4/2002 | Yagi et al. | |

FOREIGN PATENT DOCUMENTS

| | | |
|---|---|---|
| EP | 0713711 A2 | 5/1996 |
| EP | 1661596 A2 | 5/2006 |
| JP | 59-008972 A | 1/1984 |
| JP | 61-131756 A | 6/1986 |
| JP | 03-022185 B2 | 3/1991 |
| JP | 07-136271 A | 5/1995 |
| JP | 07-136272 A | 5/1995 |
| JP | 08-187289 A | 7/1996 |
| JP | 09-24098 A | 1/1997 |
| JP | 2000-325482 A | 11/2000 |
| JP | 2002-045424 A | 2/2002 |
| JP | 2002-85567 A | 3/2002 |
| JP | 2002-121010 A | 4/2002 |
| JP | 2002-143306 A | 5/2002 |
| JP | 2002-143307 A | 5/2002 |
| JP | 2001-163605 A | 6/2009 |
| WO | WO-82/01815 A1 | 6/1982 |
| WO | WO-97/11734 A1 | 4/1997 |
| WO | WO-98/18513 A1 | 5/1998 |
| WO | WO-00/23134 A1 | 4/2000 |
| WO | WO 01/04528 A1 | 1/2001 |

OTHER PUBLICATIONS

Office Action from Patent Office of the People's Republic of China for application No. 200380106490.3 dated Mar. 28, 2003.

Office Action of Japanese Patent Application No. 2002-365195 mailed on Sep. 29, 2009 (Japan).

Office Action of Korean Patent Application No. 10-2005-7011105 issued on Sep. 27, 2010 (Republic of Korea).

Supplementary European Search Report of European Patent Application No. 03780801.1 dated Nov. 2, 2009 (EPO).

* cited by examiner

OXYGEN SUPPLYING APPARATUS

TECHNICAL FIELD

The present invention relates to a respiratory oxygen supplying apparatus provided with an automatic closing valve which works according to the respiratory cycle of a user. More particularly, the present invention relates to a medical equipment to be used when a chronic respiratory disease patient or the like takes an oxygen inhalation treatment and an oxygen supplying apparatus having a function of supplying oxygen or an oxygen concentrated gas as a respiratory gas intermittently to the user according to the respiratory cycle.

BACKGROUND ART

In recent years, the number of patients who are suffered from respiratory diseases such as asthma, pulmonary emphysema and chronic bronchitis has a tendency to increase. One of the most effective therapies for these respiratory diseases is an oxygen inhalation therapy, and an oxygen concentration apparatus by which an oxygen concentrated gas is separated directly from the air, or an oxygen cylinder is becoming to be used as an oxygen supply source needed for the therapy. In the case where the oxygen inhalation therapy is done in a hospital or at home, an oxygen-enriched air supplying apparatus of a pressure variable adsorption type or a membrane type, or that using solid electrolyte membranes which selectively permeates oxygen, or a high-volume fixed-type oxygen cylinder is used.

On the other hand, when a patient goes out for attending a hospital, a portable oxygen cylinder is used. Since it is a cylinder for a respiratory disease patient to carry, the cylinder should be small-sized and light in weight, and high pressure oxygen gas is filled in it so that it can be used for a long time. The potable small-sized oxygen cylinder is provided with a pressure-reducing valve and has a flow controlling function so that oxygen can be supplied to the patient at the flow rate of the prescription.

Further, as a method for extending available time, a respiration-synchronized oxygen-supplying apparatus which has a built-in respiration sensor and an automatic closing valve, and supplies oxygen only during inhalation and not during exhalation of a patient has been proposed by JP-B 3-22185 (JP-B means Japanese examined patent publication), JP-A 59-8972 (JP-A means Japanese unexamined patent publication) or the like.

Further, the respiration-synchronized oxygen-supplying apparatus does not waste oxygen during exhalation, and it is effective also economically, and hence it was proposed to use a respiration-synchronized oxygen-supplying apparatus also in an oxygen concentration apparatus by JP-A 61-131756 or the like. Furthermore, a movable or portable oxygen concentration apparatus which can be driven by a buttery was proposed (see JP-A 7-136271, JP-A 7-136272, JP-A 2000-325482, JP-A 2002-121010 and JP-A 2002-45424), and it is desirable to equip the oxygen concentration apparatus with a respiration-synchronized oxygen-supplying apparatus in order to extend usable time, which is limited by a capacity of the buttery.

In such a respiration-synchronized oxygen-supplying apparatus, the respiration of a user is usually detected by catching nasal respiration with a pressure sensor through a cannula. Consequently, there occurs a case where the respiration is not synchronized when the respiration of a user is weak, or contrarily the respiration rate is abnormally large. There is also a case where it is not synchronized due to the deterioration of the sensor.

Further, in a case where the respiration-synchronized oxygen-supplying apparatus is used together with a portable oxygen concentration apparatus, they are sometimes used even during sleeping, in which the user sometimes breathes through the mouth, and the respiration is not detected by a usual sensor which detects only nasal respiration. In such a case, continuous oxygen supply which is independent to the respiration of the user may be required.

From this point of view, JP-A 2002-143806 proposes a structure in which the first piping system having a solenoid-operated valve and the second piping system having a setting material on which a plurality of orifices are mounted, and when the first piping system or the second piping system are selected by a switching valve, respiration synchronized oxygen supply or continuous oxygen supply can be set in oxygen flow, respectively.

DISCLOSURE OF THE INVENTION

However, differing from a conventional respiration synchronized-type oxygen supplying apparatus, a respiration synchronized-type oxygen supplying apparatus of the above-mentioned JP-A 2002-143806 requires a dual piping system consisting of an oxygen supplying piping system for continuous flow and that for respiration synchronized flow. This oxygen supplying apparatus is not preferable because the piping construction itself is complicated, and further, from the view of portability, because the oxygen supplying apparatus becomes heavy and large-sized due to the addition of a passage switching valve, a passage closing valve and a controlling system.

The present invention solves these problems and provides a respiration synchronized-type gas-supplying apparatus which can be miniaturized and has a function for setting flow rate during continuous gas supply.

The inventors of the present invention zealously studied on these problems and found that the above problems could be solved by providing a gas flow-controlling part with an automatic closing valve capable of freely controlling the aperture by electric signals. The following apparatus is provided based on this finding.

That is, the present invention relates to an oxygen supplying apparatus comprising an oxygen generating means, an oxygen-supplying means for supplying the oxygen generated by the above means to a user and an automatic closing valve placed on the oxygen-supplying passage. The oxygen-supplying apparatus is characterized in that the apparatus is provided with following units: a respiration sensor for detecting respiration of the user; a supply method setting means which selects either of continuous flow supply and supply in synchronism with the respiration of the user; a flow rate setting means for a supply flow rate; and a controlling means which controls the aperture of the automatic closing valve corresponding to the set value of the flow rate setting means by receiving supply method setting signals in the continuous flow, or opens the automatic closing valve on the inhalation starting point based on the respiration signal of the respiration sensor and at the same time controls the open time of the automatic closing valve corresponding to the flow rate set value by receiving supply method setting signals in the synchronized flow.

Further, the present invention provides an oxygen supplying apparatus characterized in the following: the automatic closing valve has a response time not more than 0.1 sec from full close to full open; and further the diameter of the orifice of the automatic closing valve is not less than 1 mmφ and no more than 5 mmφ. Furthermore, the present invention provides an oxygen supplying apparatus which is characterized in that an oxygen-generating means is a pressure-variable adsorption-type oxygen concentrating means provided with an adsorption cylinder packed with an absorbent which selectively absorbs nitrogen more than oxygen and a compressor which supplies pressurized air to the adsorption cylinder.

BEST MODE FOR CARRYING OUT THE INVENTION

Figure 1:
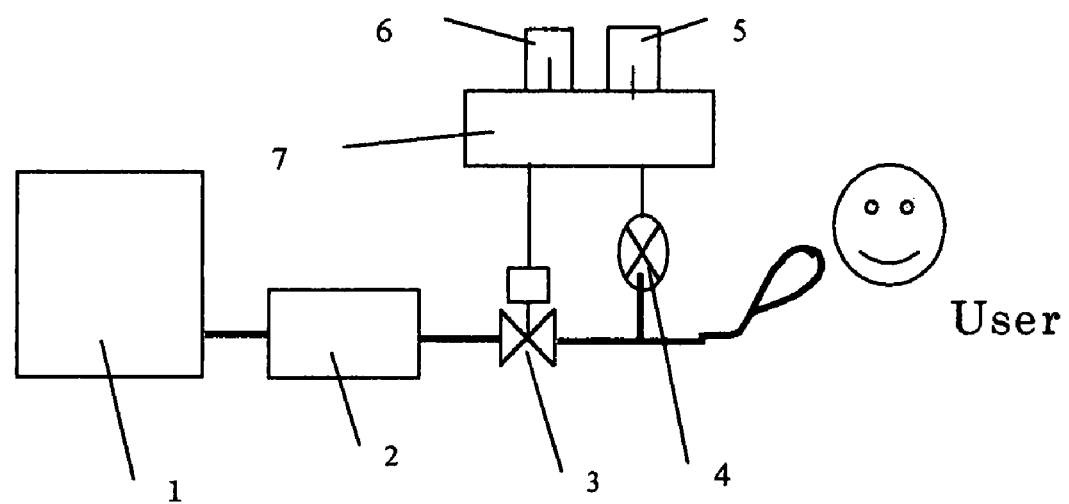
FIG. 1 is a construction drawing of an oxygen supplying apparatus of the present invention.

The present invention relates to an oxygen supplying apparatus comprising an oxygen generating means, an oxygen-supplying means for supplying the oxygen generated by the above means to a user and an automatic closing valve placed on the oxygen-supplying passage, and further relates to an oxygen supplying apparatus provided with an automatic closing valve having a function capable of continuously controlling the aperture by electric signals on a gas flow-controlling part.

Here, the oxygen generating means is an apparatus capable of continuously supplying oxygen, and the examples of the oxygen generating means include an oxygen concentrating means of a selectively oxygen-permeating membrane type, an adsorptive type or an electrochemical type with an electrolyte, an oxygen cylinder, a liquefied oxygen filled container, and the like.

The oxygen concentrating means of a selectively oxygen-permeating membrane type is an apparatus in which a polymer membrane whose oxygen permeation coefficient is larger than the nitrogen permeation coefficient is placed, and air is supplied under pressure on one side of the membrane by a compressor or the like, and concentrated oxygen is taken out from the other side of the membrane. The examples of the polymer membrane include membranes of polydimethylsiloxane-polycarbonate copolymer, poly(4-methylpentene-1), polyphenylene oxide, porphyrin complex or the like.

The adsorption-type oxygen concentrating means includes a pressurized-type means, a depressurized-type means, and an combination of the pressurized-type means and the depressurized-type means. In the pressurized-type means, oxygen is concentrated by alternately operating an adsorption process in which oxygen-concentrated gas is obtained by introducing pressurized air using a compressor or the like into adsorption beds having a packed adsorbent which can adsorb nitrogen selectively to allow nitrogen to be adsorbed in a pressurized state and a desorption process in which the adsorbent is regenerated by reducing the inner pressure of the adsorption beds to allow the nitrogen to be desorbed. In the depressurized-type means, oxygen is concentrated by alternately operating a process in which nitrogen is adsorbed by introducing atmospheric air into adsorption beds under normal pressure and a desorption process in which the adsorbent is regenerated by reducing the inner pressure of the adsorption beds from normal pressure by gas suction with a vacuum pump or the like to allow the nitrogen to be desorbed. The adsorbent is exemplified by a molecular sieve of crystalline zeolite having selective adsorptivity to nitrogen. As the zeolite, a zeolite having a metal element as a cation is preferable. A concrete example includes the following: a sodium zeolite which is a 5A-type or a 13X-type zeolite; a lithium zeolite which is a X-type zeolite having a $SiO_2/Al_2O_3$ ratio of 2.0-3.0 and at the same time a crystalline zeolite at least 88% of whose $AlO_4$ tetrahedral unit associates with lithium cation; and the like.

Further, the electrochemical-type oxygen concentrating means using an electrolyte is exemplified by the following: an oxygen concentrating means in which an oxygen-ion conductive solid electrolyte is used, air is supplied on one side of the solid electrolyte by a blower or the like to reduce oxygen to an oxygen ion, the oxygen ion is transported to the other side of the solid electrolyte, and the oxygen ion is oxidized to oxygen; an oxygen concentrating means in which a proton conductive polymer electrolyte is used, and oxygen is transported from one side to the other side in the same manner; and the like.

The oxygen cylinder is a high pressure cylinder in which the gas to be used is filled under high pressure, wherein the gas is filled usually at 15 MPa to 20 MPa of the inner pressure. The liquefied oxygen-filled container is a container in which a substance having a gaseous state at room temperature is deeply cooled to a liquid state, and the liquefied substance is filled in a heat-insulating container. When the liquefied oxygen comes out from the container through a gas outlet on use, it is gasified by the ambient temperature so that the oxygen can be taken out as gas.

Examples of the respiration sensor for detecting the respiration of a user include a pressure sensor, a flow rate sensor, a gas sensor and the like. The pressure sensor is a condenser formed with a diaphragm comprising a conductive film, silicon and the like, and an electrode placed in a state of facing the diaphragm. The diaphragm is deformed proportionally to the pressure change, and the deformation is detected by the change of the electrostatic capacity of the condenser. Thus, the respiration of a user is detected by the pressure change in the vicinity of the sensor due to the respiration. As the flow rate sensor, a heating coil-type flow sensor is used. The flow rate is determined from the amount of heat taken out by gas flow at the heating coil, and the respiration of a user is detected by the change of flow rate determined by this sensor. The gas sensor is exemplified by a sensor which uses a semiconductor or the like whose resistance changes according to the gas density around the periphery of the sensor, and in which the gas density around the periphery of the sensor is determined from the changes of the resistance. Thus, the respiration is detected from the changes of the gas density of the respiration in a user (the oxygen concentration decreases during exhalation).

An apparatus of the present invention is provided with a supply method setting means capable of selecting either of a continuous flow supplying method in which oxygen is supplied to a user in continuous flow and a synchronized supply method in which oxygen is supplied in synchronism with the respiration of a user. Further, it is provided with a flow rate setting means capable of setting the flow rate of a prescription, that is, the flow rate of oxygen to be supplied to the user. The setting signals for these two setting means are taken into a controlling means which controls opening and closing of an automatic closing valve, and thereby the aperture, open time and timing of the automatic closing valve are controlled. This controlling means is an electric circuit capable of receiving the above-mentioned setting signals, and calculating and controlling the aperture, open time, timing and the like of the automatic closing valve according to the setting signals by using a specified circuit.

When the controlling means receives a supply method setting signal for continuous flow, the aperture of the automatic closing valve is controlled so that it corresponds to the set value of the flow rate setting means. Further, when the controlling means receives a supply method setting signal for synchronized flow, the automatic closing valve is opened on the inhalation starting point based on the respiration signal of the respiration sensor, and at the same time the open time of the automatic closing valve is controlled so that it corresponds to the flow rate set value.

The automatic closing valve is constructed with a spring, an iron core having a valve function and an electromagnetic coil which is wound around the periphery of the iron core. The iron core keeps the valve in the full close state or the full open state by the force of the spring when no voltage is applied on the iron core. On the other hand, when an arbitrary voltage is applied on the iron core, the iron core is kept at a midway between the full open position and the full close position under the balance of the forces of the spring and the electromagnetic field induced by the electromagnetic coil. Thus, the aperture of the automatic closing valve is controlled, so that the flow rate of the gas passing through the valve can be controlled.

In such an automatic closing valve, a rapid response speed is required from the necessity of oxygen supply to a patient as quickly as possible, and in the case of the gas supply in the respiration synchronized method, a response time from the start of inhalation of a patient to the start of oxygen supply, that is, from the full close state to the full open state of the valve is preferably 0.1 sec or less. When the response time is longer than 0.1 sec, the gas supply on the start of inhalation is extremely delayed in the synchronized oxygen supply. More preferably, it is 0.02 sec or less.

The gas flow rate which is needed by a common user is in the range of 250-7000 cm$^3$/min. When an adsorption-type oxygen concentrating means is used as the gas supplying apparatus, it being difficult to give a high pressure to oxygen like the case of a high pressure cylinder, the gas pressure is usually about 0.1 MPa in a relative pressure at the highest. Consequently, in order to enable the control of the flow rate in the above range, the diameter of the orifice of the automatic closing valve having an aperture controlling function is preferably 0.2 mm$\phi$ to 5 mm$\phi$. When the diameter is smaller than 0.2 mm$\phi$, it is difficult to obtain the flow rate up to 7000 cm$^3$/min due to a pressure loss. On the other hand, when the diameter is larger than 5 mm$\phi$, the flow rate controlling accuracy is deteriorated at the slow flow, that is, at 250 cm$^3$/min during a continuous flow. The diameter of the orifice is preferably 1-5 mm$\phi$, and more preferably 1-3 mm$\phi$.

The use of an aperture controlling-type valve like this enables either of synchronized and continuous oxygen supply controls to be performed, and it is effective for miniaturizing a respiration synchronization-type oxygen supplying apparatus. Enabling a simple structure comprising one flow passage and one automatic closing valve to be constructed, this system affords an easily operable flow passage structure and is suitable for miniaturization.

The oxygen supply method setting means does not care about methods such as electric setting or mechanical setting, and any means is acceptable so long as it can transmit a selected electric signal to the controlling means.

In the case where the respiration synchronized oxygen supply method is selected, the full open state and the full close state are repeated by electric signals in synchronism with the inhalation of a user according to a set flow rate. The length of the full open state is calculated by a controlling means according to the process of the respiration synchronization method, the set flow rate and the information on the state of respiration of the user detected by the sensor.

The respiration synchronization method is roughly divided into two kinds of processes: a fixed saving ratio process and a fixed pulse process. In the case of the fixed saving ratio process, the time of the full open state is set in such a manner that it does not depend on the frequency of respiration per unit time of a user, but the total amount per unit time of the gas supplied to the user becomes constant, that is, when the respiration rate is small, the time of the full open state per one inhalation is made long, and it is shortened in inverse proportion to the increase of the respiration rate. Thus, the saving ratio of the gas can be kept constant regardless the respiration rate of the user.

In the case of the fixed pulse process, the length of time of the full open state for one inhalation is kept constant independently of the respiration rate, and the total amount of the gas to be supplied to a user per unit time is increased with the increase of the respiration rate. In this case, the expected value of the saving ratio decreases with the increase of the respiration rate of the user. The method of the present invention can cope with any of the respiration synchronization processes.

On the other hand, when the continuous gas supply method is selected, the aperture of the automatic closing valve is continuously controlled by electric signals according to the set flow rate.

Incidentally, in the case of using an adsorption-type oxygen concentrating means as the oxygen supplying apparatus, the pressure of the oxygen to be supplied varies periodically due to the method of a pressure variable type in which adsorption and desorption are repeated. Consequently, it is preferable to place a tank for temporarily storing the product of oxygen at some place of the oxygen supply piping from the oxygen supply means to the automatic closing valve with the object of suppressing pressure variation.

EXAMPLE

Hereafter, the present invention will be explained with FIG. 1.

As an oxygen supply means 1, a pressure-variable adsorption-type oxygen concentrating means was used. It was a 4-cylinder-type VPSA oxygen concentrator provided with 4 adsorption cylinders filled with crystalline zeolite which was a X-type zeolite having a $SiO_2/Al_2O_3$ ratio of 2.0-3.0 and at least 88% of the $AlO_4$ tetrahedral unit of the zeolite was associated with lithium cations as adsorbent, wherein the adsorption cylinders generated oxygen by serially switching adsorption and desorption by using a rotary valve. Here, the pressure of the oxygen generated from the adsorption beds varied in the range of 10 kPa to 100 kPa. The fluctuation of the pressure was relieved by once supplying the oxygen to a tank 2 having a capacity of 300 cm$^3$, and then the oxygen was supplied to an automatic closing valve 3 having an aperture controlling function. Here, the average pressure of the tank 2 was 30 kPa and the width of the fluctuation of the pressure became 10-60 kPa.

As an automatic closing valve 3, a VSO valve (PNEUTRONICS-™ Voltage Sensitive Orifice Proportional Solenoid Valve) of VSONC series manufacture by Parker Hannifin was used. The speed of response of the automatic closing valve 3 was 0.008 sec in terms of the time from the sending of an electric signal to the start of opening of the valve. As a respiration detection sensor 4, a micro differential pressure transmitter KL17-111-30DY manufactured by Nagano Keiki was used.

Figure 2:
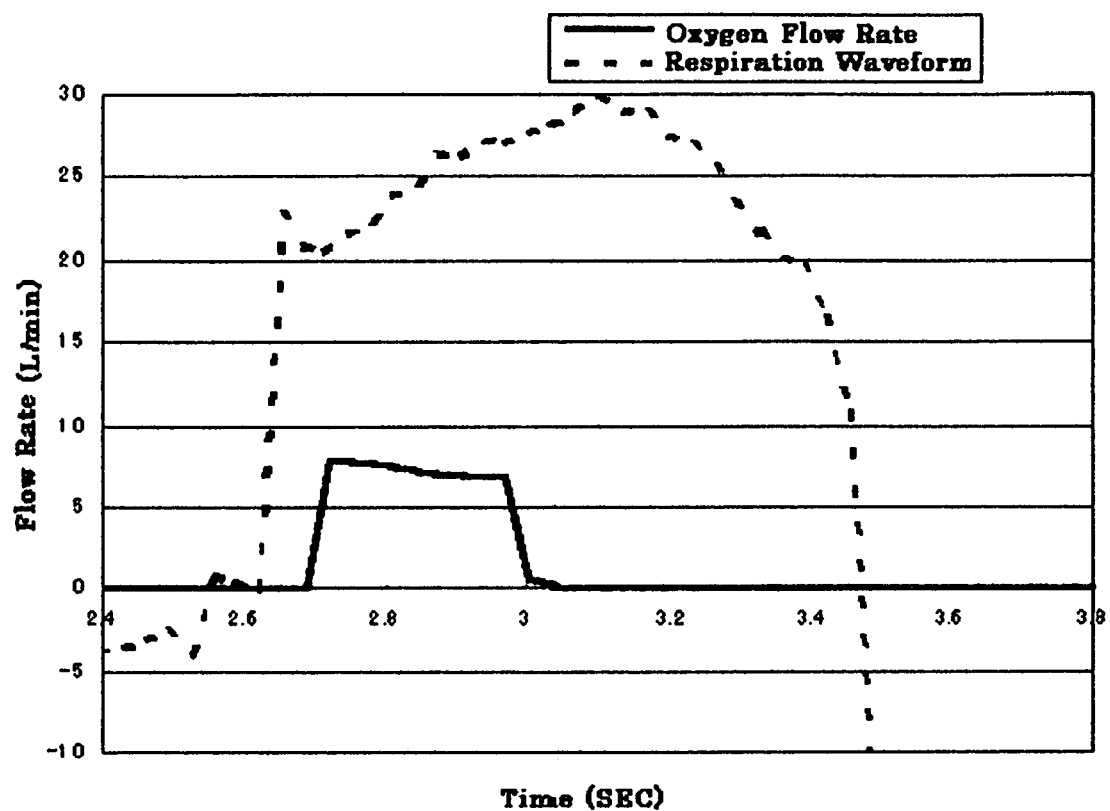
FIG. 2 shows the result of oxygen supply during respiration synchronized flow using an oxygen supplying apparatus of the present invention.

The automatic closing valve 3 was controlled by a controlling part 7 which had taken the information set by an oxygen supply method setting means 6 and an oxygen flow rate setting means 5. In the present example, a fixed saving ratio process was used as a respiratory synchronization method, and the ratio was set at 2/3. The respiration synchronization method was selected by the oxygen supply method setting means 6. The oxygen supply pattern was determined on TTL model lung manufactured by Michigan Instrument with a flow meter under the conditions of the respiration rate of 20 per min and the flow rate of 2000 $cm^3$/min. The flow meter was placed on the air way part of the model lung, and the results of the measurement are shown in FIG. 2. It was made clear by the figure that oxygen supply started at about 0.08 sec from the beginning of inhalation, and oxygen was supplied instantaneously responding inhalation.

Figure 3:
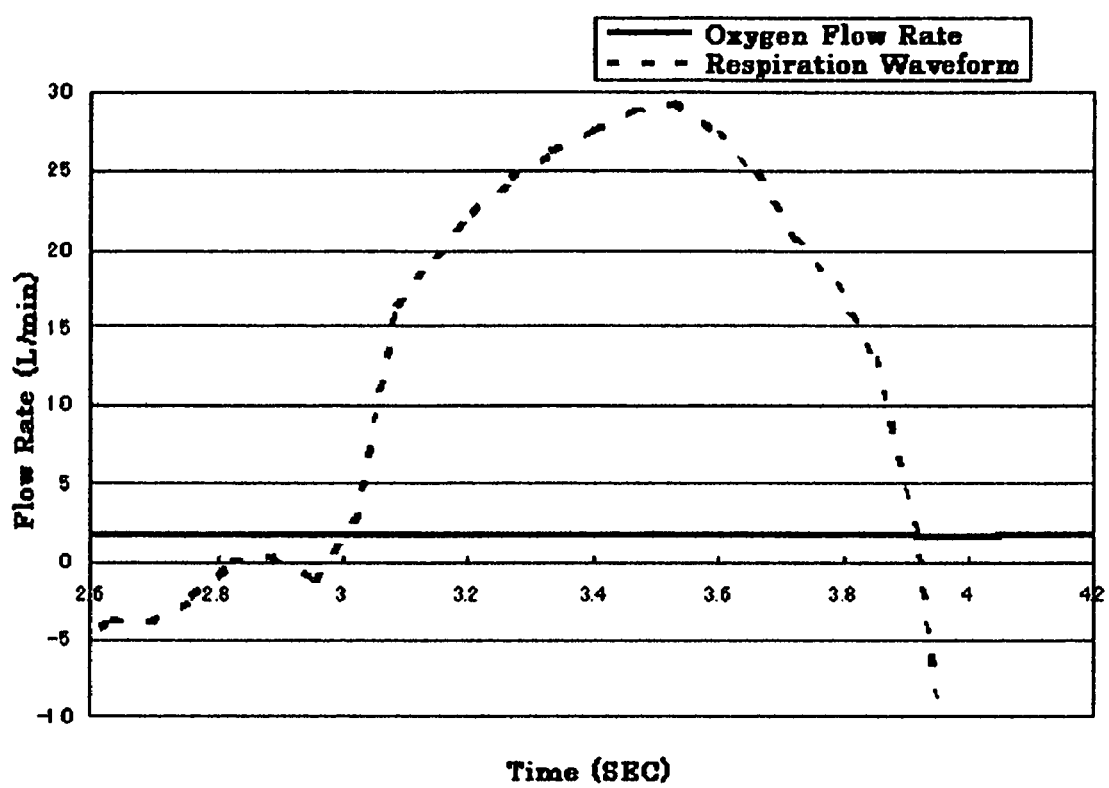
FIG. 3 shows the result of oxygen supply during continuous flow using an oxygen supplying apparatus of the present invention.

On the other hand, a continuous flow method was set by the oxygen supply method setting means 6, and the flow rate was determined under the same condition as the synchronized flow. The results are shown in FIG. 3. It was made clear by the figure that oxygen was continuously supplied under the control of flow rate at 2000 $cm^3$/min. Although the data are not shown, it is possible to control the flow rate in the range of 250-5000 $cm^3$/min.

Effect of the Invention

The present invention provides a respiration synchronized-type gas supplying apparatus which has a function for setting the flow rate during continuous supply and at the same time can be miniaturized by simplifying the structure.

The invention claimed is:

1. An oxygen supplying apparatus comprising an oxygen generating means, an oxygen supplying means for supplying the oxygen generated by the oxygen generating means to a user and a single automatic closing valve placed on an oxygen-supplying passage, wherein the oxygen supplying apparatus comprising:
   a respiration sensor which detects the respiration of the user and provides a respiration signal;
   a supply method setting means which selects the supply in a continuous flow or the supply in synchronism with the respiration of the user;
   a flow rate setting means for setting a supply flow rate set value; and,
   a controlling means which controls an aperture of said single automatic closing valve corresponding to the supply flow rate set value of the flow rate setting means by receiving a supply method setting signal of the continuous flow, or opens said single automatic closing valve on the inhalation starting point based on the respiration signal of the respiration sensor by receiving a supply method setting signal of the synchronous flow and at the same time controls the open time of said single automatic closing valve corresponding to the flow rate set value, wherein said single automatic closing valve is controlled by the controlling means which had taken the information set by the supply method setting means and the flow rate setting means.

2. The oxygen supplying apparatus according to claim 1, wherein said single automatic closing valve has a response time from a full close state to a full open state of 0.1 sec or less.

3. The oxygen supplying apparatus according to claim 1 or 2, wherein the orifice of said single automatic closing valve is not less than 1 mm in diameter and not larger than 5 mm in diameter.

4. The oxygen supplying apparatus according to claim 1, wherein the oxygen generating means is a adsorption oxygen concentrating means provided with adsorption cylinders packed with adsorbent which adsorbs selectively nitrogen rather than oxygen and a compressor which supplies pressurized air to the adsorption cylinders.

5. An oxygen supplying apparatus comprising an oxygen generating means, an oxygen supplying means for supplying the oxygen generated by the oxygen generating means to a user and a single automatic closing valve placed on an oxygen-supplying passage, wherein the oxygen supplying apparatus comprising:
   a respiration sensor which detects the respiration of the user and provides a respiration signal;
   a supply method setting means which selects the supply in a continuous flow or the oxygen supply in synchronism with the respiration of the user;
   a flow rate setting means for setting a supply flow rate set value; and,
   a controlling means which controls an aperture of said single automatic closing valve based upon the supply flow rate set value of the flow rate setting means by receiving a supply method setting signal of the continuous flow, or opens said single automatic closing valve on the inhalation starting point based on the respiration signal of the respiration sensor by receiving a supply method setting signal of the synchronous flow and at the same time controls the open time of said single automatic closing valve corresponding to the flow rate set value, wherein the supply method setting means and the flow rate setting means are composed separately and independently.

6. The oxygen supplying apparatus according to claim 5, wherein said single automatic closing valve has a response time form a full close state to a full open state of 0.1 sec or less.

7. The oxygen supplying apparatus according to claim 5 or 6, wherein the orifice of said single automatic closing valve is not less than 1 mm in diameter and not larger than 5 mm in diameter.

8. The oxygen supplying apparatus according to claim 5, wherein the oxygen generating means is an adsorption oxygen concentrating means provided with adsorption cylinders packed with adsorbent which adsorbs selectively nitrogen rather than oxygen and a compressor which supplies pressurized air to the adsorption cylinders.

* * * * *